US007001368B2

(12) United States Patent
Otsubo (10) Patent No.: US 7,001,368 B2
(45) Date of Patent: Feb. 21, 2006

(54) DISPOSABLE PULL-ON WEARING ARTICLE (75) Inventor: Toshifumi Otsubo, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/983,894

(22) Filed: Oct. 26, 2001

(65) Prior Publication Data
US 2002/0052588 A1    May 2, 2002

(30) Foreign Application Priority Data
Oct. 31, 2000    (JP)    ............................. 2000-332677

(51) Int. Cl.
A61F 13/15    (2006.01)
A61F 13/20    (2006.01)
(52) U.S. Cl. ........................... 604/385.3; 604/385.201; 604/396
(58) Field of Classification Search ........... 604/385.01, 604/385.207, 385.21–385.31, 392–396, FOR 103, 604/FOR 104; 53/429, 436
See application file for complete search history.

(56) References Cited
U.S. PATENT DOCUMENTS

| | | | | |
|---|---|---|---|---|
| 2,097,903 A | * | 11/1937 | Wallis | .................. 604/373 |
| 2,201,255 A | * | 5/1940 | Wilson, Jr. | .................. 604/394 |
| 2,493,113 A | * | 1/1950 | Dance | .................. 604/394 |
| 2,505,891 A | * | 5/1950 | Grogan | .................. 604/394 |
| 2,545,216 A | * | 3/1951 | Toussie | .................. 604/394 |
| 2,664,895 A | * | 1/1954 | Shulman | .................. 604/366 |
| 3,860,003 A | * | 1/1975 | Buell | .................. 604/385.25 |
| 4,205,679 A | * | 6/1980 | Repke et al. | .................. 604/366 |
| 4,244,367 A | * | 1/1981 | Rollenhagen | .................. 604/396 |
| 4,338,938 A | * | 7/1982 | Seavitt | .................. 604/377 |
| 4,642,110 A | * | 2/1987 | Dudek | .................. 604/385.21 |
| 4,694,978 A | * | 9/1987 | Westphal et al. | .................. 223/28 |
| 4,747,846 A | * | 5/1988 | Boland et al. | .................. 604/385.22 |
| 4,847,134 A | * | 7/1989 | Fahrenkrug et al. | .................. 428/138 |
| 4,909,804 A | * | 3/1990 | Douglas, Sr. | .................. 604/385.29 |
| D345,015 S | * | 3/1994 | Booth | .................. D24/126 |
| 5,340,424 A | * | 8/1994 | Matsushita | .................. 156/164 |
| 5,383,871 A | * | 1/1995 | Carlin et al. | .................. 604/385.29 |
| 5,441,493 A | * | 8/1995 | Gonzalez-Anguiano Marsel et al. | .................. 604/394 |
| 5,695,488 A | * | 12/1997 | Sosalla | .................. 604/385.24 |
| 5,725,518 A | * | 3/1998 | Coates | .................. 604/391 |
| 5,836,930 A | * | 11/1998 | Lantz et al. | .................. 604/378 |
| D403,401 S | * | 12/1998 | Bernard et al. | .................. D24/126 |
| 5,858,012 A | * | 1/1999 | Yamaki et al. | .................. 604/385.27 |
| 6,213,991 B1 | * | 4/2001 | Kling et al. | .................. 604/385.01 |
| 6,702,798 B1 | * | 3/2004 | Christoffel et al. | ... 604/385.201 |
| 2002/0068919 A1 | * | 6/2002 | Shinohara et al. | ..... 604/385.27 |
| 2002/0072728 A1 | * | 6/2002 | Shinohara et al. | ..... 604/385.29 |
| 2002/0183706 A1 | * | 12/2002 | Valentin et al. | ........ 604/385.01 |

FOREIGN PATENT DOCUMENTS

EP    0452951 A1 *    4/1991

(Continued)

Primary Examiner—Karin Reichle
(74) Attorney, Agent, or Firm—Lowe Hauptman & Berner, LLP (57) ABSTRACT A disposable pull-on wearing article folded along a folding zone extending across a crotch region in a transverse direction so that the inner surface of the article comes in contact with itself. The folding zone is formed at a position displaced toward a front waist region so that a front peripheral edge portion of a waist-opening defined by the front waist region lies at a longitudinally lower position than that of a rear peripheral edge portion of the waist-opening defined by a rear waist region.

8 Claims, 6 Drawing Sheets

FOREIGN PATENT DOCUMENTS

| | | |
|---|---|---|
| EP | 0 847 739 A2 | 6/1998 |
| GB | 2245149 A * | 1/1992 |
| JP | 64-6105 A * | 1/1989 |
| JP | 3021190 B | 11/1995 |
| WO | WO 91/08725 | 6/1991 |
| WO | WO 9428845 A1 * | 12/1994 |
| WO | WO 97/33815 | 9/1997 |
| WO | WO 9960971 A1 * | 12/1999 |

* cited by examiner

DISPOSABLE PULL-ON WEARING ARTICLE

BACKGROUND OF THE INVENTION

This invention relates to a disposable pull-on wearing article such as a disposable pants-type diaper, training pants or disposable pants for incontinent patients.

Japanese Utility Model Application Publication No. 3021190B discloses a structure of foldable disposable pants. The pants described in the Publication basically comprise a liquid-pervious topsheet, a liquid-impervious backsheet and a liquid-absorbent core disposed between these two sheets so as to define a waist-opening and a pair of leg-openings.

In the disclosed pants, one of transversely opposite lateral regions extending between front and rear waist regions is tucked inwardly of the pants so as to be disposed between these waist regions. The other of the transversely opposite lateral regions is folded back onto the outer surface of one of the front and rear waist regions. As each of transversely opposite lateral regions is folded in a direction of the center of the waist regions of the pants, the pants in the folded up state have a substantially rectangular shape.

To unfold the pants from the folded up state, the peripheral edge portion of the waist-opening defined by the front waist region and the peripheral edge portion of the waist-opening defined by the rear waist region must be held by fingers and pulled away from each other to widen the waist-opening of the pants. These two peripheral edge portions overlap and are joined to each other, so it is not easy to insert the thumbs of both hands into the space between the peripheral edge portions and, correspondingly, wearing the pants takes much time.

SUMMARY OF THE INVENTION

It is an object of this invention to provide a disposable pull-on wearing article improved to be foldable so that peripheral edge portions of the waist-opening defined by the front and rear waist regions can be picked up without inserting the thumbs of both hands into the space between the peripheral edge portions of the waist-opening.

According to this invention, there is a disposable pull-on wearing article comprising front and rear waist regions opposed to each other and a crotch region positioned between these waist regions so as to define a waist-opening and a pair of leg-openings.

The disposable article is folded up along a folding zone extending across the crotch region in a transverse direction so that an inner surface of the article comes in contact with itself, wherein the folding zone is formed at a position displaced toward one of the front waist region and the rear waist region so that one of front and rear peripheral edge portions of the waist-opening defined respectively by the front and rear waist regions lies at a position lower than the other.

According to one preferred embodiment of this invention, each of transversely opposite regions extending in a waist-surrounding direction and being defined by both the front and rear waist regions is tucked inwardly of the article so as to be disposed between the remainder of the front and rear waist regions.

DETAILED DESCRIPTION OF THE PREFERRED EMBODIMENT

Details of a disposable pull-on wearing article according to this invention will be more fully understood from the description given hereunder with reference to the accompanying drawings.

Figure 1:
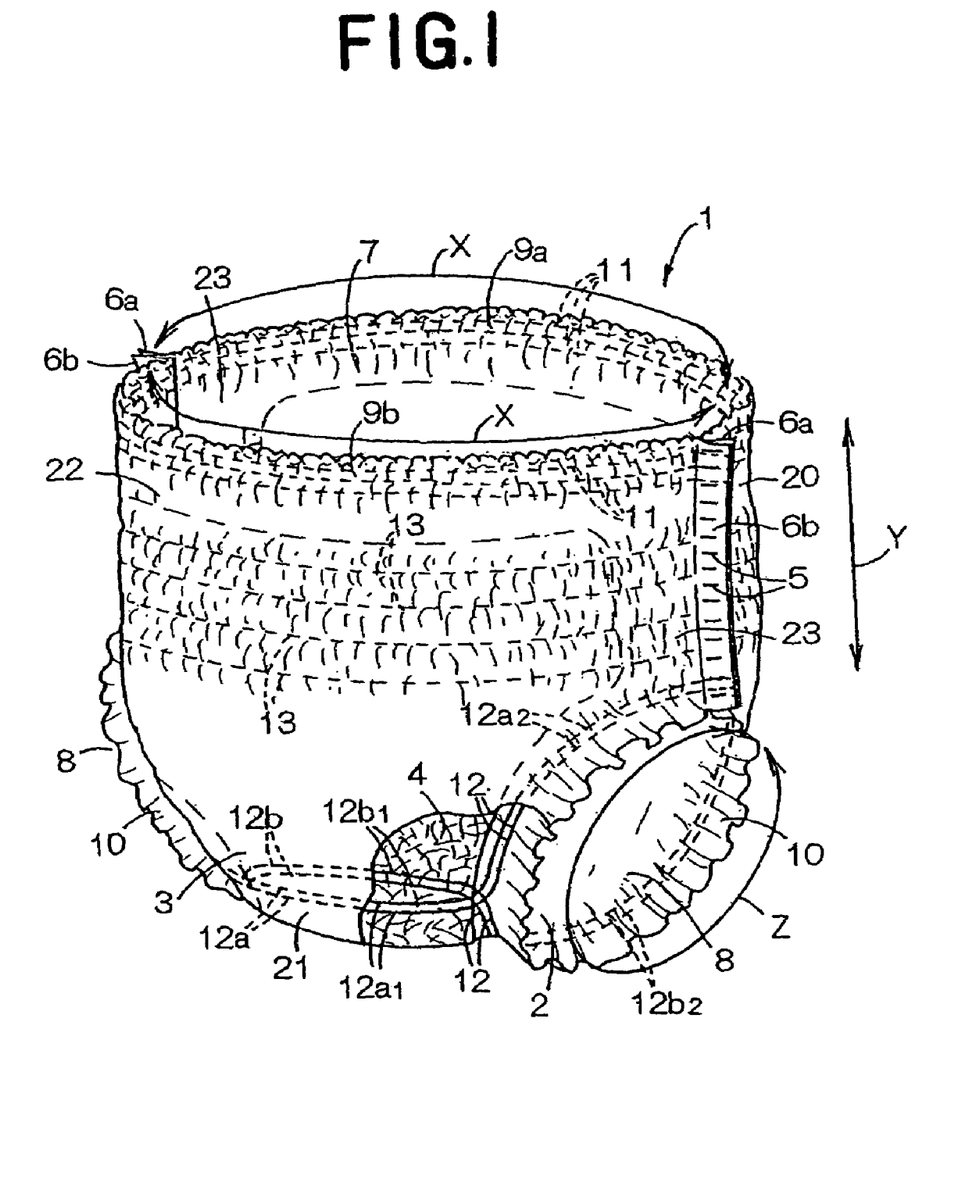
FIG. 1 is a perspective view showing a partially cutaway disposable diaper as viewed from the rear waist region.
Figure 2:
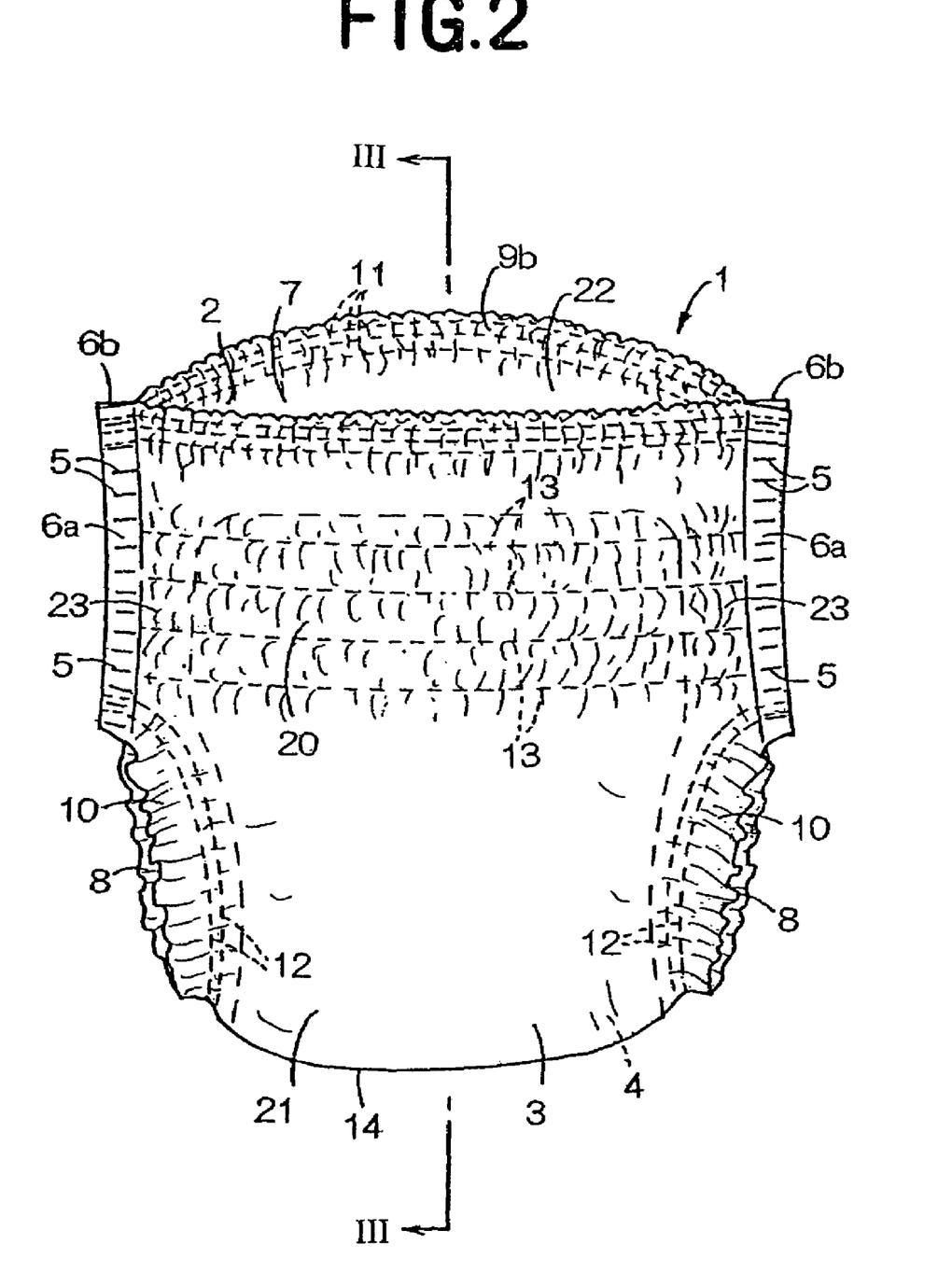
FIG. 2 is a perspective view showing the same diaper in folded state as viewed from the side of a front waist region.
Figure 3:
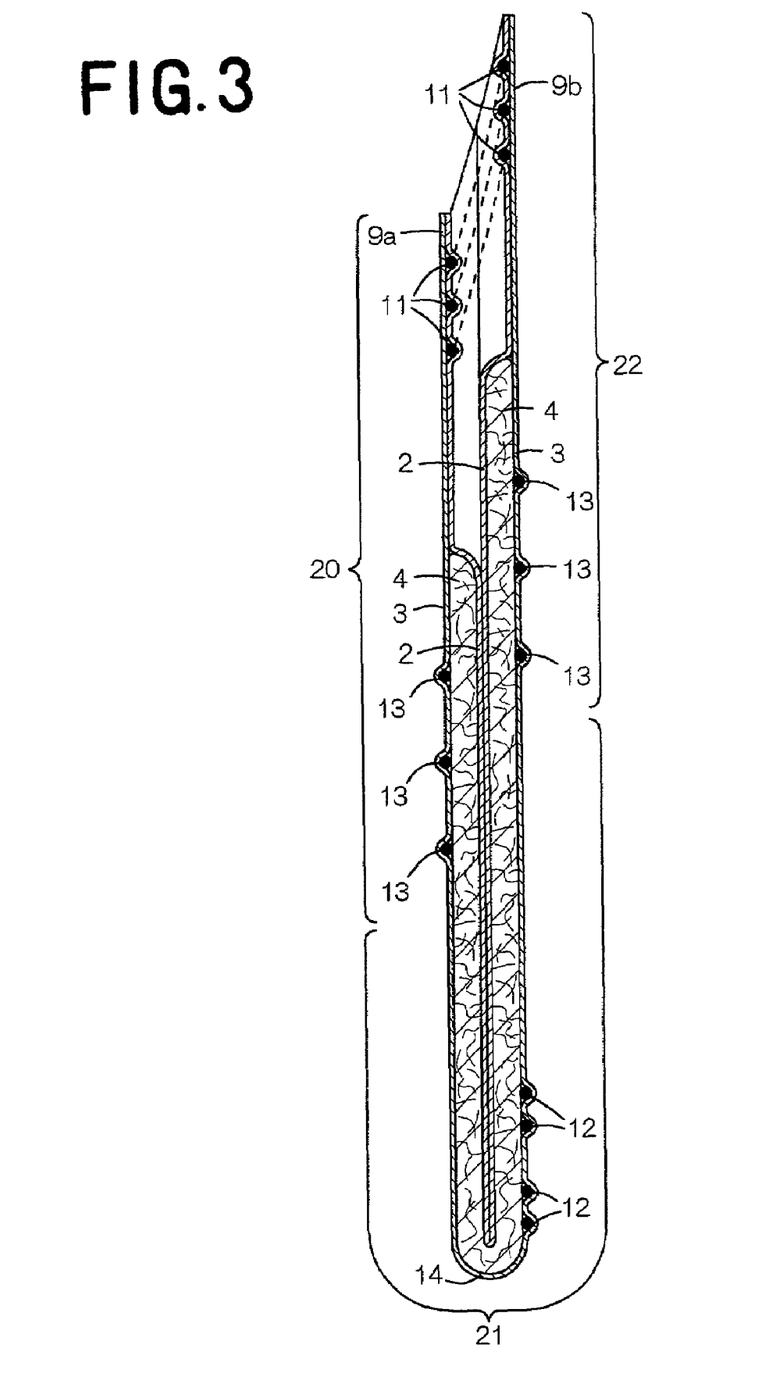
FIG. 3 is a sectional view taken along a line III—III in FIG. 2.

FIG. 1 is a perspective view showing a partially cutaway disposable pull-on diaper 1, FIG. 2 is a perspective view showing the diaper 1 in its folded state as viewed from the side of a front waist region 20 and FIG. 3 is a sectional view taken along a line III—III in FIG. 2. In FIG. 1, a waist-surrounding direction is indicated by an arrow X, a longitudinal direction is indicated by an arrow Y and a thigh-surrounding direction is indicated by an arrow Z. It should be understood that the surfaces of top- and backsheets 2, 3 facing a core 4 will be hereinafter referred to as inner surfaces of the sheets 2, 3 and the surfaces of the top- and backsheets 2, 3 not facing the core 4 will be hereinafter referred to as outer surfaces of the sheets 2, 3.

The diaper 1 basically includes the liquid-pervious topsheet 2, the liquid-impervious backsheet 3 and the liquid-absorbent core 4 disposed between these sheets 2, 3 and entirely covered with and bonded to tissue paper (not shown). The core 4 is bonded to the inner surfaces of the topsheet 2 and the backsheet 3 with the tissue paper therebetween.

The diaper 1 is composed of front and rear waist regions 20, 22 opposed to each other and a crotch region 21 positioned between these front and rear waist regions 20, 22. The front and rear waist regions 20, 22 respectively have transversely opposite side edge portions 6a, 6b. These side edge portions 6a, 6b are overlaid like inter-locked hands and bonded intermittently at a plurality of spots 5 arranged in the longitudinal direction. The front and rear waist regions, in the vicinity of the bonded side edge portions 6a, 6b, together define transversely opposite lateral regions 23. Thereupon, a waist-opening 7 and a pair of leg-openings 8 are also defined by the front and rear waist regions and the crotch region.

The diaper 1 further includes transversely opposite lateral regions 23 extending in the waist-surrounding direction between the front and rear waist regions 20, 22 defined by connecting the front and rear waist regions 20, 22 to each other along the respective side edge portions 6a, 6b. Thereupon, a waist-opening 7 and a pair of leg-openings 8 are also defined.

Along front and rear peripheral edge portions 9a, 9b of the waist-opening 7 defined by the front and rear waist regions 20, 22 respectively, elastic members 11 each comprising a plurality of elastic elements and stretchable in the waist-surrounding direction are disposed between the top- and backsheets 2, 3 and bonded under tension to the inner surfaces of these sheets 2, 3.

Along peripheral edge portions 10 of the leg-openings 8, elastic members 12 each comprising a plurality of elastic elements and stretchable in the thigh-surrounding direction are disposed between the top- and backsheets 2, 3 and bonded under tension to the inner surfaces of these sheets 2, 3.

Elastic members 12 associated with the leg-openings comprise a first elastic member 12a and a second elastic member 12b associated with the respective leg-openings. These first and second elastic members 12a, 12b have central sections $12a_1$, $12b_1$ extending across the crotch region 21 in the transverse direction and end sections $12a_2$, $12b_2$ extending along the peripheral edge portions 10 of the associated leg-openings 8. The end sections $12a_2$ of the first elastic member 12a extend along substantially rear halves the peripheral edge portions 10 of the associated leg-openings 8 and the end section $12b_2$ of the second elastic member 12b extend along substantially front halves of the peripheral edge portions 10 of the associated leg-openings 8.

Between the elastic members 11 associated with the waist-opening and the elastic members 12 associated with the leg-openings, a plurality of auxiliary elastic members 13 stretchable in the waist-surrounding direction are disposed between the top- and backsheets 2, 3 and bonded under tension to the inner surfaces of the sheets 2, 3. FIG. 1 shows a state in which a plurality of gathers are formed along the front and rear peripheral edge portions 9a, 9b of the waist-opening 7, the peripheral edge portions 10 of the respective leg-openings 8 and the front and rear waist regions 20, 22 as the elastic members 11, 12, 13 contract themselves, respectively.

As will be apparent from FIG. 2, the diaper 1 is folded along a folding zone 14 extending across the crotch region 21 in the transverse direction so that the outer surface of the topsheet 2 (i.e., the inner surface of the diaper 1) comes in contact with itself. The folding zone 14 is formed at a position appropriately displaced toward the front waist region 20. With the diaper 1 folded along such folding zone 14, the front peripheral edge portion 9a of the waist-opening 7 defined by the front waist region 20 lies at a position longitudinally lower than that of the rear peripheral edge portion 9b of the waist-opening 7 defined by the rear waist region 22.

With the diaper 1 having the front and rear peripheral edge portions 9a, 9b of the waist-opening 7 lying at different positions, the rear peripheral edge portion 9b can be easily held by the fingers without trouble in inserting the thumbs of both hands into the space between the front and rear peripheral edge portions 9a, 9b. The waist-opening 7 is slightly widened and the front peripheral edge portion 9a is spaced from the rear peripheral edge portion 9b as the rear peripheral edge portion 9b is held by the fingers. Consequently, the front peripheral edge portion 9a can be easily held by the fingers. Now both the front peripheral edge portion 9a and the rear peripheral edge portion 9b may be separately held by the fingers of both hands and pulled in opposite directions to space one from another to further widen the waist-opening 7 of the diaper 1 in a folded up state.

Figure 4:
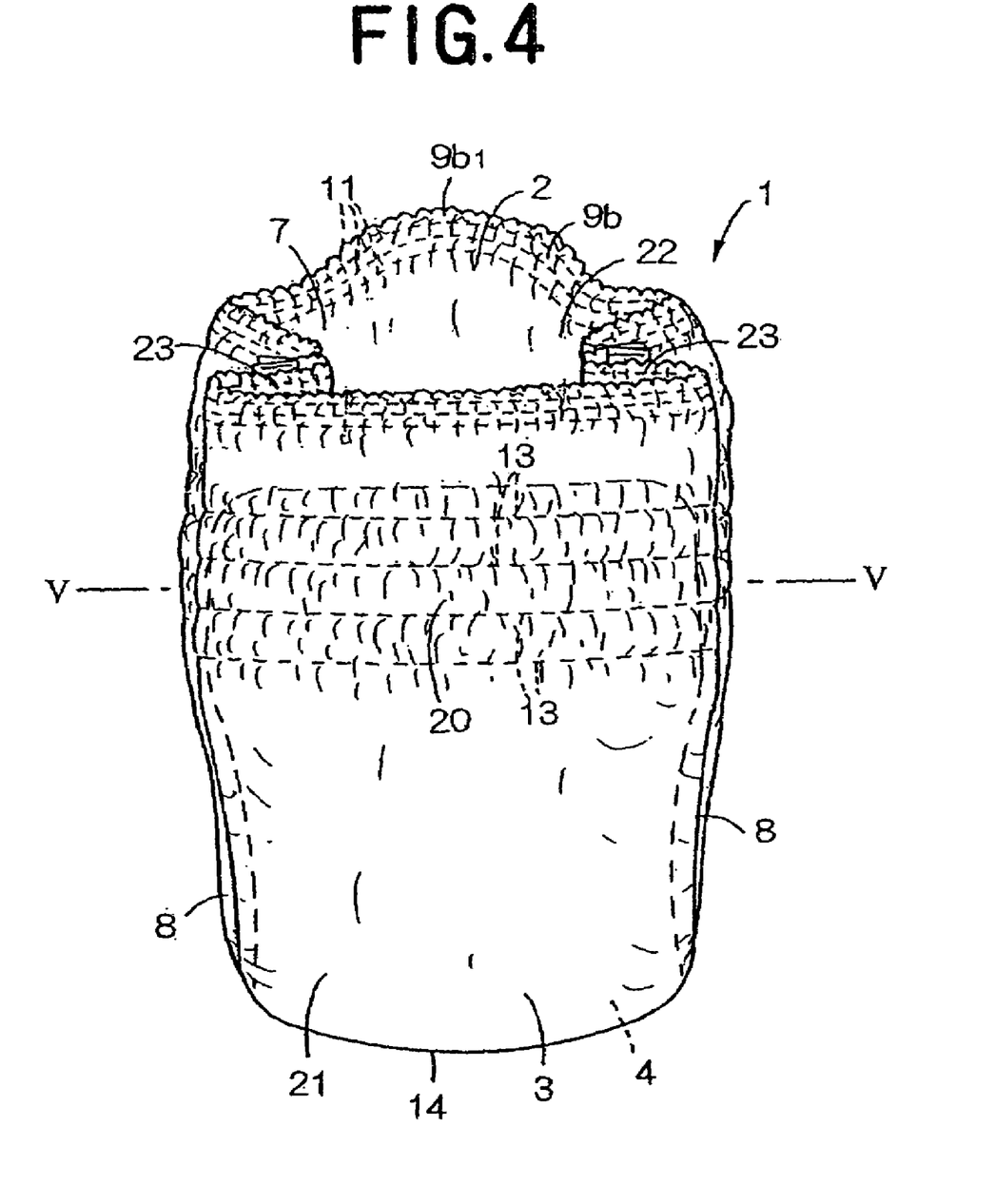
FIG. 4 is a perspective view showing the diaper of FIG. 2 as having been further folded up.
Figure 5:
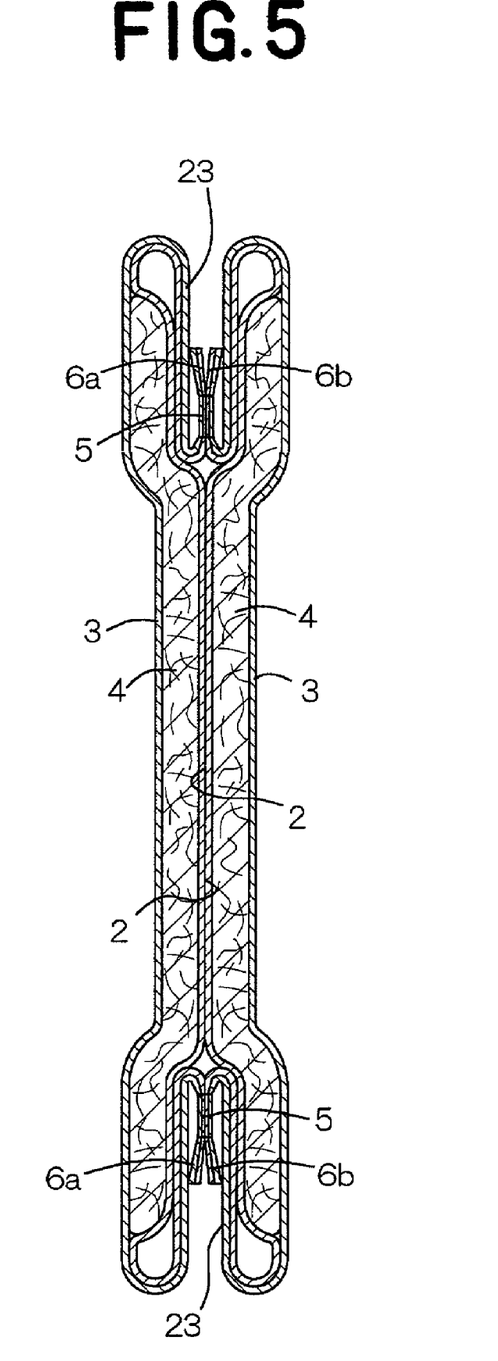
FIG. 5 is a sectional view taken along a line V—V in FIG. 4.
Figure 6:
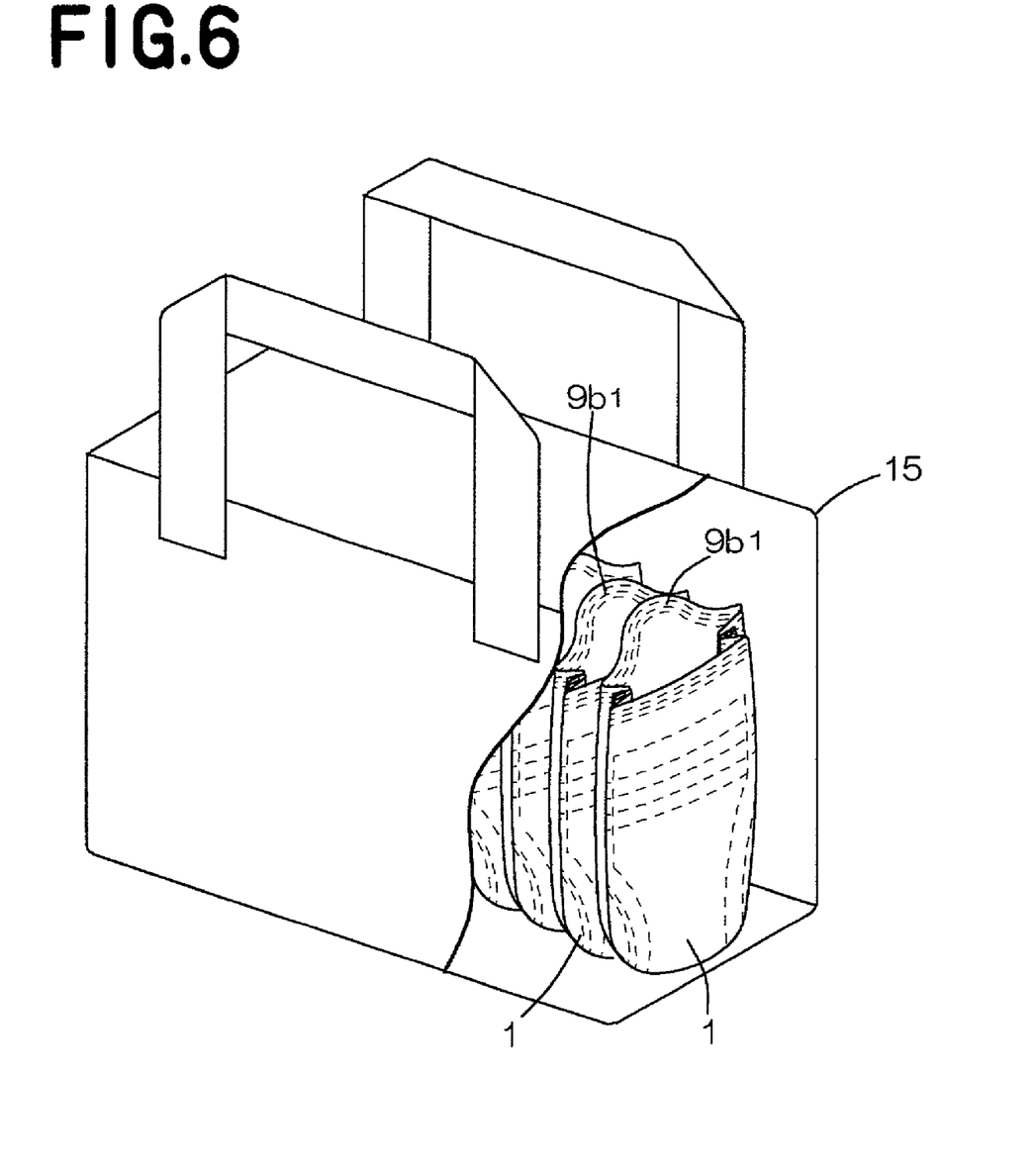
FIG. 6 is a perspective view showing a package containing therein a plurality of the diapers each shown in FIG. 4.

FIG. 4 is a perspective view showing the diaper 1 of FIG. 2 as having been further folded up, FIG. 5 is a sectional view taken along a line V—V in FIG. 4 and FIG. 6 is a perspective view showing a package 15 containing therein a plurality of the diapers 1 each shown in FIG. 4. The transversely opposite lateral regions 23 are tucked inwardly of the diaper 1 so that these lateral regions 23 are disposed between the remainder of the front and rear waist regions 20, 22. The rear peripheral edge portion 9b of the waist-opening 7 defined by the rear waist region 22 has its transversely middle section $9b_1$ extending upward beyond the front peripheral edge portion 9a of the waist-opening 7 defined by the front waist region 20.

Tucking of the lateral regions 23 inwardly of the diaper 1 enables the diaper 1 to be made more compact in size than the diaper 1 in the state shown in FIG. 2. The middle section $9b_1$ of the rear peripheral edge portion 9b serves as a grip which may be held by the fingers to hold the rear peripheral edge portion 9b without the troublesome operation of inserting the thumbs of both hands into the space between the front and rear peripheral edge portions 9a, 9b. For this diaper 1, the front peripheral edge portion 9a may be held by the fingers after the middle section $9b_1$ of the rear peripheral edge portion 9b has been held.

As seen in FIG. 6, a plurality of the diaper 1 may be packed in the package 15 with one diaper closely placed one another. The middle sections $9b_1$ of the respective rear peripheral edge portions 9b extend upward beyond the front peripheral edge portions 9a so that the individual diaper 1 may be taken out from the package 15 merely by holding the middle section $9b_1$ of the rear peripheral edge portion 9b. In this way, operation of taking the diaper 1 out from the package 15 is facilitated.

While the folding zone 14 illustrated in the accompanied fingers extending across the crotch region 21 in the transverse direction is provided at the position displaced toward the front waist region 20, it is also possible to provide the folding zone 14 at the position displaced toward the rear waist region 22. With the diaper 1 having the folding zone 14 formed at the position displaced toward the rear waist region 22, the rear peripheral edge portion 9b of the waist-opening 7 defined by the rear waist region 22 lies at a longitudinally lower position than that of the front peripheral edge portion 9a of the waist-opening 7 defined by the front waist region 20.

From the package 15 within which a plurality of the diaper 1 according to the embodiment illustrated in FIG. 2 are closely packed one upon another, the individual diaper 1 can be easily pulled out with the rear peripheral edge portion 9b of the waist-opening 7 defined by the rear waist region 22 held by fingers since this rear peripheral edge portion 9b extends upward beyond the front peripheral edge portion 9a of the waist-opening 7 defined by the front waist region 20.

The topsheet 2 may be formed by a hydrophilic fibrous nonwoven fabric or a porous plastic film. The backsheet 3 may be formed by a hydrophobic fibrous nonwoven fabric, a liquid-impervious plastic film or a laminated composite sheet of hydrophobic nonwoven fabric and plastic film. The backsheet 3 may be also formed by a composite nonwoven fabric consisted of a melt blown fibrous nonwoven fabric having a high water-resistant property sandwiched by two layers of spun bond nonwoven fabric having high strength and flexibility.

The nonwoven fabric may be selected from a group including spun lace-, needle punch-, melt blown-, thermal bond-, spun bond-, chemical bond- and air through-nonwoven fabric. Component fiber of the nonwoven fabric may be selected from a group including polyolefine-, polyester- and polyamide-based fibers and polyethylene/polypropylene or polyethylene/polyester core-sheath type conjugated fiber and side-by-side-type conjugated fiber.

The core 4 is a mixture of fluff pulp, high absorption polymer particles and thermoplastic synthetic resin fibers compressed to a desired thickness. The polymer particles may be selected from a group including starch-, cellulose-based polymer and synthetic polymer.

To bond the top- and backsheets 2, 3 to each other, to bond the core 4 to the top- and backsheets 2, 3 and to attach the elastic members 11, 12, 13 to the diaper 1, suitable adhesives such as hot melt adhesives or welding means like heat-sealing or ultrasonic sealing may be used.

The pants-type disposable wearing article according to this invention includes the folding zone extending across the crotch region in the transverse direction. This folding zone is formed at the position displaced toward any one of the front and rear waist regions so that one of the front and rear peripheral edge portions of the waist-opening defined by these two waist regions may lie at a longitudinally lower position than that of the other as the diaper is folded up. This unique arrangement advantageously eliminates the troublesome operation of inserting the thumbs of both hands into the space between the front and rear peripheral edge portions of the waist-opening defined by the front and rear waist regions, respectively. Specifically, the above-mentioned unique arrangement enables the waist-opening to be widened merely by holding one of the front and rear peripheral edge portions with the fingers and then holding the other in the same manner.

With the article having its lateral regions tucked inwardly of the article so as to be disposed between the front and rear waist regions and one of the front and rear peripheral edge portions of the waist-opening defined by the front and rear waist regions lying at a longitudinally lower position than that of the other, the transversely middle section of the one peripheral edge portion extends upward beyond the other peripheral edge portion. Such feature enables the waist-opening to be widen merely by holding the transversely middle section with the finger and then by holding the other peripheral edge portion in the same manner.

From the package containing therein a plurality of these articles, the individual article can be easily taken out therefrom merely by pulling the individual article out from the package with the one peripheral edge portion or the transversely middle section thereof held with the fingers.

What is claimed is:

1. A disposable pull-on wearing article in a folded state, said folded article comprising, in a longitudinal direction, front and rear waist regions opposed to each other, and bonded along side edge portions thereof, and a crotch region positioned between said front and rear waist regions so as to define a waist-opening and a pair of leg-openings, the waist-opening having front and rear peripheral edges which are defined by said front and rear waist regions, respectively;
   wherein
   said article is folded along a folding zone extending across said crotch region in a transverse direction so that an inner surface of said article comes in contact with itself;
   said folding zone is closer to one of said front and rear peripheral edges than the other so that said front and rear peripheral edges of said waist-opening lie at different elevations in said longitudinal direction;
   said article further comprises front and rear waist-opening elastic members extending circumferentially of said waist-opening in said front and rear waist regions, respectively, said front and rear waist-opening elastic members being substantially equally spaced, in said longitudinal direction, from said front and rear peripheral edges, respectively; and
   said article has a relaxed, unfolded state in which the front and rear waist-opening elastic members are coelevational throughout an entire circumferential extent of said waist opening.

2. The folded article of claim 1, wherein transversely opposite lateral regions defined in combination by said front and rear waist regions are tucked inwardly of the folded article so as to be disposed between remainders of said front and rear waist regions.

3. The folded article of claim 2, wherein the front peripheral edge of the waist-opening extends substantially straight between the inwardly tucked lateral regions and is closer to said folding zone than said rear peripheral edge.

4. The folded article of claim 3, wherein the rear peripheral edge describes a curve curved away from the front peripheral edge in the longitudinal direction.

5. A pack of a plurality of folded disposable pull-on wearing articles;
   each of said folded article comprising, in a longitudinal direction, front and rear waist regions opposed to each other, and bonded along side edge portions thereof, and a crotch region positioned between said front and rear waist regions so as to define a waist-opening and a pair of leg-openings, the waist-opening having front and rear peripheral edges which are defined by said front and rear waist regions, respectively;
   wherein
   said article is folded along a folding zone extending across said crotch region in a transverse direction so that an inner surface of said article comes in contact with itself;
   said folding zone is closer to one of said front and rear peripheral edges than the other so that said front and rear peripheral edges of said waist-opening lie at different elevations in said longitudinal direction;
   said folded article further comprises front and rear waist-opening elastic members extending circumferentially of said waist-opening in said front and rear waist regions, respectively, said front and rear waist-opening elastic members being substantially equally spaced, in said longitudinal direction, from said front and rear peripheral edges, respectively; and
   said article has a relaxed, unfolded state in which the front and rear waist-opening elastic members are coelevational throughout an entire circumferential extent of said waist opening.

6. The pack of claim 5, wherein transversely opposite lateral regions defined in combination by said front and rear waist regions are tucked inwardly of the folded article so as to be disposed between remainders of said front and rear waist regions.

7. The pack of claim 6, wherein the front peripheral edge of the waist-opening of each said folded article extends substantially straight between the inwardly tucked lateral regions and is closer to said folding zone than said rear peripheral edge.

8. The pack of claim 7, wherein, in each said folded article, the rear peripheral edge describes a curve curved away from the front peripheral edge in the longitudinal direction.

* * * * *